(12) United States Patent
Pak

(10) Patent No.: US 10,251,909 B2
(45) Date of Patent: Apr. 9, 2019

(54) POTASSIUM-MAGNESIUM CITRATE AS A SURROGATE OF THE DASH DIET IN MANAGING HYPERTENSION

(75) Inventor: Charles Y. C. Pak, Dallas, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 1197 days.

(21) Appl. No.: 11/673,497

(22) Filed: Feb. 9, 2007

(65) Prior Publication Data
US 2008/0193525 A1    Aug. 14, 2008

(51) Int. Cl.
*A61K 33/00* (2006.01)
*A61K 31/19* (2006.01)
*A61K 33/06* (2006.01)
*A61K 45/06* (2006.01)
*A23L 33/16* (2016.01)

(52) U.S. Cl.
CPC .............. *A61K 33/00* (2013.01); *A23L 33/16* (2016.08); *A61K 31/19* (2013.01); *A61K 33/06* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,473,595 A * | 9/1984 | Rood et al. | 426/649 |
| 5,219,889 A * | 6/1993 | Walsdorf et al. | 514/574 |
| 5,424,074 A * | 6/1995 | Koli et al. | 424/464 |
| 5,432,200 A | 7/1995 | Walsdorf et al. | |
| 5,804,204 A * | 9/1998 | Morris et al. | 424/439 |
| 6,136,349 A | 10/2000 | Karppanen et al. | |
| 6,287,607 B2 * | 9/2001 | Pak et al. | 424/682 |
| 6,808,726 B2 * | 10/2004 | Hojo et al. | 426/74 |
| 6,881,750 B2 | 4/2005 | Boynton | |
| 7,015,250 B2 * | 3/2006 | Clouatre | A61K 31/194 514/557 |
| 7,091,246 B2 | 8/2006 | Rushforth | |
| 2004/0224076 A1 | 11/2004 | Derrien et al. | |
| 2005/0123670 A1 | 7/2005 | Vasquez | |
| 2008/0206412 A1 * | 8/2008 | Leclerc | 426/271 |

FOREIGN PATENT DOCUMENTS

| | | |
|---|---|---|
| CN | 1207294 | 2/1999 |
| JP | 1300874 | 12/1989 |
| JP | 6343417 | 12/1994 |
| WO | 90/00522 A1 | 1/1990 |
| WO | 95/07630 A1 | 3/1995 |
| WO | 2005/094615 A1 | 10/2005 |
| WO | WO 2006097629 A1 * | 9/2006 |

OTHER PUBLICATIONS

Potassium, http://www.jctonic.com/include/minerals/potassiu.htm, 2004 (accessed Dec. 18, 2010).*
Szelenyi et al. "Effect of magnesium orotate and orotic acid on experimental hypertension and cardiopathogenic changes in heart muscle", Deutsches Medizinisches Journal, 1970, vol. 21, issue 22, pp. 1405-1406, 1409-1410, and 1412; English Abstract.*
Ferrannini et al., NEJM, 1987, vol. 317, pp. 350-357.*
Abate N, Chandalia M, Cabo-Chan AV Jr, Moe OW, Sakhaee K. The metabolic syndrome and uric acid nephrolithiasis: novel features of renal manifestations of insulin resistance. Kid Int 65: 386-392, 2004.
Akita S, Sacks FM, Svetkey LP, et al. Effects of the dietary approaches to stop hypertension (DASH) diet on the pressure-natriuresis relationship. Hypertension 42: 8-13, 2003.
Appel LJ, Champagne CM, Harsha DW, Cooper LS, Obarzanek E, Elmer PJ, Stevens VJ, Vollmer VM, Lin PH, Svetkey LP, Stedman SW, Young DR, Writing Group of the PREMIER Collaborative Research Group. Effects of comprehensive lifestyle modification on blood pressure control: main results of the PREMIER clinical trial. J Am Med Ass 289: 2083-2093, 2003.
Aviv A, Hollenberg NK, Weder A. Urinary potassium excretion and sodium sensitivity in blacks. Hypert 43: 707-713, 2004.
Conlin PR, Erlinger TP, Bohannon A, Miller ER 3rd, Appel LJ, Svetkey LP, Moore TJ. The DASH diet enhances the blood pressure response to losartan in hypertensive patients. Am J Hypert 16: 337-342, 2003.
Harano Y, Suzuki M, Koyama Y, Kanda M, Yasuda S, Suzuki K, Takamizawa I. Multifactorial insulin resistance and clinical impact in hypertension and cardiovascular diseases. J Diab Compl 16: 19-23, 2002.
Klisic J, Hu MC, Nief V, Reyes L, Fuster D, Moe OW, Ambuhl PM. Insulin activates Na(+)/H(+) exchanger 3: biphasic response and glucocorticoid homeostasis. Am J Physiol 283: F532-F539, 2002.
Lin PH, Aickin M, Champagne C, Craddick S, Sacks FM, McCarron P, Most-Windhauser MM, Rukenbrod F, Haworth L; DASH-Sodium Collaborative Research Group. Food group sources of nutrients in the dietary patterns of the DASH-Sodium trial. J Am Diet Assoc 103: 488-496, 2003.
Maalouf NM, Sakhaee K, Parks JH, Coe FL, Adams-Huet B, Pak CYC. Association of urinary pH with body weight in nephrolithiasis. Kid Int 65: 1422-1425, 2004.
Nowson CA, Worsley A, Margerison C, Jorna MK, Godfrey SJ, Booth A. Blood pressure change with weight loss is affected by diet type in men. A J Clin Nutr 81: 983-989, 2005.
Odvina CV, Preminger GM, Lindberg JS, Moe OW, Pak CYC. Long-term combined treatment with thiazide and potassium citrate in nephrolithiasis does not lead to hypokalemia or hypochloremic metabolic alkalosis. Kid Int 63: 240-247, 2003.
Odvina CV, Mason RP, Pak CYC. Prevention of thiazide-induced hypokalemia without magnesium depletion by potassium-magnesium citrate. Am J Therap 13: 101-108, 2006.

(Continued)

*Primary Examiner* — Jeffrey S Lundgren
*Assistant Examiner* — Stephanie K Springer
(74) *Attorney, Agent, or Firm* — Norton Rose Fulbright US LLP

(57) ABSTRACT

The present invention includes compositions and methods for using a single pharmaceutical preparation of KMgCit is a convenient surrogate or to support the DASH diet in lowering blood pressure among patients with essential hypertension. Support is provided by potassium, magnesium and alkali, which overcome the underlying physiological-biochemical disturbances of essential hypertension, such as salt sensitivity, insulin resistance, low urinary pH, low serum magnesium and renal leak of calcium. Positive effects of KMgCitrate disclosed in normal subjects and patients with stones, provides assurance that KMgCitrate should ameliorate the above physiological-biochemical disturbances and associated disorders in patients with essential hypertension.

7 Claims, 2 Drawing Sheets

(56) References Cited

OTHER PUBLICATIONS

Ogihara T, Asano T, Ando K, et al. High-salt diet enhances insulin signaling and induces insulin resistance in Dahl salt-sensitive rats. Hypertension 40: 83-89, 2002.

Pamidimukkala J & Jandhyala BS. Effect of salt rish diet in the obese Zucker rats: studies on renal function during isotonic volume expansion. Clin Exper Hypert 26: 55-67, 2004.

Resnick LM, Oparil S, Chait A, et al. Factors affecting blood pressure responses to diet: the Vanguard study. Am J Hypert 13: 956-965, 2000.

Sacks FM, Svetkey LP, Vollmer WM, Appel LJ, Bray GA, Harsha D, Obarzanek E, Conlin PR, Miller ER 3rd, Simons-Morton DG, Karanja N, Lin PH; DASH-Sodium Collaborative Research Group. Effects on blood pressure of reduced dietary sodium and the Dietary Approaches to Stop Hypertension (DASH) diet. DASH-Sodium Collaborative Research Group. N Engl J Med 344: 3-10, 2001.

Sakhaee K, Adams-Huet B, Moe OW, Pak CYC. Pathophysiologic basis for normouricosuric uric acid nephrolithiasis. Kid Int 62: 971-979, 2002.

Schmidlin O, Tanaka M, Bollen AW, Yi SL, Morris RC Jr. Chloride-dominant salt sensitivity in the stroke-prone spontaneously hypertensive rat. Hypertension 45: 867-873, 2005.

Sellmeyer DE, Schloetter M, Sebastian A. Potassium citrate prevents increased urine calcium excretion and bone resorption induced by a high sodium chloride diet. J Clin Endocrinol Metab 87: 2008-2012, 2002.

Suter PM, Sierro C, Vetter W. Nutritional factors in the control of blood pressure and hypertension. Nutr Clin Care 5: 9-19, 2002.

Vollmer VM, Sacks FM, Ard J, Appel LJ, Bray GA, Simons-Morton DG, Conlin PR, Svetkey LP, Erlinger TP, Moore TJ, Karanja N; DASH-Sodium Trial Collaborative Research Group. Effects of diet and sodium intake on blood pressure: subgroup analysis of the DASH-sodium trial. Ann Inter Med 135: 1019-1028, 2001.

\* cited by examiner

POTASSIUM-MAGNESIUM CITRATE AS A SURROGATE OF THE DASH DIET IN MANAGING HYPERTENSION

TECHNICAL FIELD OF THE INVENTION

The present invention relates in general to the field of treatments for hypertension, and more particularly, to compositions and methods for supplementing a Dietary Approaches to Stop Hypertension (DASH) diet.

BACKGROUND OF THE INVENTION

Without limiting the scope of the invention, its background is described in connection with calcium supplements and dietary supplementation. Two patents (U.S. Pat. Nos. 5,432,200 & 5,219,889), in which the inventor of this patent served as a co-inventor, are patents that teach methods for manufacture of calcium supplements. While one of these patents teaches a composition that may include KMgCitrate as a dietary supplement of potassium and magnesium specific mentions to disease conditions is lacking. A follow-up patent (U.S. Pat. No. 7,091,246 B2) offered improved process of making KMgCitrate, again with only reference to general dietary supplementation.

PCT/SE89/00410 and PCT/EP94/03072 advocated a palatable salt substitute to be added to food, instead of a tablet pharmaceutical formulation as with KMgCitrate. The active ingredient is entirely different from KMgCitrate; it is composed of "carnallite" and "kainite," which are chloride and/or sulfate salts of potassium and magnesium without any citrate. Unlike KMgCitrate, these "double salts" do not confer an alkali load; thus, they neither correct the metabolic disturbances of undue urinary acidity of gouty diathesis nor possess antihypertensive action of alkali discussed above. The blood pressure lowering effect of these salt substitutes may be ascribed to the reduced intake of sodium (from the substitution of table salt) and other additives whose purpose or actions are poorly described.

US 2004/0224076 A1 recommended a salt substitute rather than a pharmaceutical preparation as with KMgCitrate. Rather than a single compound, it is a mixture, which contains additional substances not present in KMgCitrate (sodium, chloride, and calcium). Its principal component is potassium salt of chloride rather than citrate. Thus, it is devoid of desirable alkalinizing action. Hypotensive effect of such salt substitute, inferred but not directly tested, can be explained by reduced intake of substituted salt.

U.S. Pat. No. 6,136,349 teaches a method of making food seasoning or food ingredient, by adding mixtures of salts as well as plant sterols and/or stanols. The mixture contains calcium (absent in KMgCitrate), and has potassium and magnesium as non-citrate salts. The claims of this invention may be applicable to experimental rats, but not necessarily to human beings.

US 2005/0123670 A1 is a liquid preparation to be used as a seasoning, rather than a tablet formulation. Unlike KMgCitrate, it contains calcium and incorporates potassium chloride rather than potassium citrate. No mention was made of its use in the management of hypertension.

PCT/US2004/006349 is a method for making a food seasoning of agreeable taste, rather than a tablet formulation as with KMgCitrate. It contains a mixture of salts, including a calcium salt and sodium chloride, which are absent in KMgCitrate. Magnesium is present as magnesium sulfate, an insoluble salt of poor bioavailability. It describes the process of making but does not mention use in hypertension.

U.S. Pat. No. 6,881,750 B2 is a composition comprising potassium taurate bicarbonate and/or potassium taurate ascorbate—substances that are entirely different than KMgCitrate. It was tested in experimental rats given a high salt diet, not in human beings.

JP1300874 is a method for "nourishing" food items such as soybean or gluten by adding various salts. Calcium is added as a bone meal, a poorly soluble calcium phosphate. JP6343417 includes a salt seasoning that contains sodium, calcium, potassium and magnesium as chloride salts. Thus, they differ from KMgCitrate, a citrate salt of potassium and magnesium to be used as a tablet pharmaceutical preparation.

CN1090483C is features a method for making a tablet preparation containing potassium and magnesium. However, it is clearly not the same as KMgCitrate of the present invention. Potassium is present as a chloride salt, which does not confer an alkali load and which is believed to be not as effective as potassium alkali in controlling high blood pressure (Morris et al., Semin Nephrol 19: 487-493, 1999). It incorporates magnesium as a chloride or sulfate salt. While magnesium chloride is soluble, it confers an acid load (rather than an alkali load provided by KMgCitrate); acid load can cause bone loss, low urinary citrate and propensity for stone formation. Magnesium sulfate is poorly soluble and sparingly bioavailable. Three case reports are presented to support the claim in hypertension. However, none of the cases can be professed to be convincing.

SUMMARY OF THE INVENTION

This invention includes compositions and methods for treating hypertension by providing potassium, magnesium and alkali, given as a single preparation of KMgCitrate. By virtue of having a similar mineral composition as the DASH that has been shown to be effective in lowering blood pressure, KMgCitrate represents a convenient and safe way of managing essential hypertension.

A method is presented for treating essential hypertension by using potassium-magnesium citrate (KMgCitrate) as a single pharmaceutical formulation. This method is based on the well-known finding that the so-called DASH diet (in rich in fruits, vegetables, nuts and dairy products, and limited in fat content) lowers blood pressure through the combined effects of three key dietary components—potassium, magnesium and alkali, all of which are provided by KMgCitrate. This invention may be used to support or enhance the blood pressure-lowering effect of the DASH diet may be more conveniently served by orally administered KMgCitrate.

High blood pressure occurring without any obvious cause is sometimes called essential hypertension. Essential hypertension may be a part of the "metabolic syndrome," which describes a complex combination of disorders associated with obesity, such as hypertension, type II diabetes, and kidney stones (Sakhaee et al., Kid Inter 62: 971-979, 2002). Thus, patients with essential hypertension are prone to suffer from various metabolic disturbances, such as salt sensitivity (avid accumulation of salt that raises blood pressure), insulin resistance (that leads to type II diabetes), low urinary pH (unusually acid urine causing uric acid stones), and hypercalciuria (high urinary calcium that can cause calcium stones).

Evidence is provided that KMgCitrate may correct or ameliorate the above cited metabolic disturbances. In so doing, this invention may not only help control high blood pressure, but improve diabetic control and reduce propensity for kidney stones.

The effect of KMgCitrate on blood pressure was tested in normal subjects who were given hydrochlorothiazide concurrently for 5 months. KMgCitrate produced a significant reduction in blood pressure as early as one month and for as long as 5 months. However, potassium chloride had no statistically significant effect on blood pressure.

The present invention includes compositions and methods for treating essential hypertension, by providing a patient in need thereof a nutritionally effective amount of a dietary supplement comprising potassium, magnesium and citrate. The preparation may be a potassium-magnesium citrate, e.g., with a molar ratio of 1:1:1 to 4:1:2. The potassium-magnesium citrate may be made at different molar ratios, to achieve daily intake of 10-80 mmoles potassium per day, 2.5-20 mmoles magnesium per day, and 5-40 mmol citrate per day. The potassium-magnesium citrate preparation may be a tablet, powder or liquid preparation, and where the essential ingredients in the preparation are from a discrete compound or a mixture of potassium citrate and magnesium citrate.

The present invention also includes a method for providing bioavailable potassium and magnesium as well as alkali by administration of a pharmaceutical preparation, in order to treat essential hypertension by providing a patient in need thereof a pharmaceutically effective amount of potassium, magnesium and citrate. The composition will generally have a blood pressure-lowering effect equal to that of the DASH diet using a single pharmaceutical preparation instead of diet.

Another method of the present invention ameliorates or corrects metabolic disturbances that often accompany essential hypertension, including salt retention, insulin resistance, unusually acid urine, low serum magnesium and renal hypercalciuria by providing a patient in need thereof a pharmaceutically effective amount of potassium, magnesium and citrate. The amelioration or correction of the metabolic disturbances treats essential hypertension and one or more symptoms selected from co-existing disease conditions of the metabolic syndrome, including type II diabetes, uric acid stones and calcium stones. Other metabolic disturbances of essential hypertension are ameliorated or corrected by potassium-magnesium citrate with a supplement having potassium-magnesium citrate with a molar ratio of 1:1:1 to 4:1:2.

Another embodiment is a method for treating patients with hypertension who are taking potassium-losing diuretics, by providing a pharmaceutical preparation of potassium-magnesium citrate. In specific examples, the pharmaceutical preparation reduces hypokalemia from diuretic treatment is reduced by a potassium-magnesium citrate dietary supplement, hypomagnesemia from diuretic therapy is reduced by a potassium-magnesium citrate dietary supplement and/or enhances blood pressure-lowering effects of diuretics.

The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
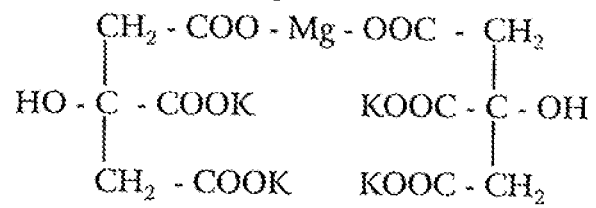
FIG. 1 graphically illustrates the empirical formula of KMgCitrate, with a molar ratio of 4:1:2.
Figure 2:
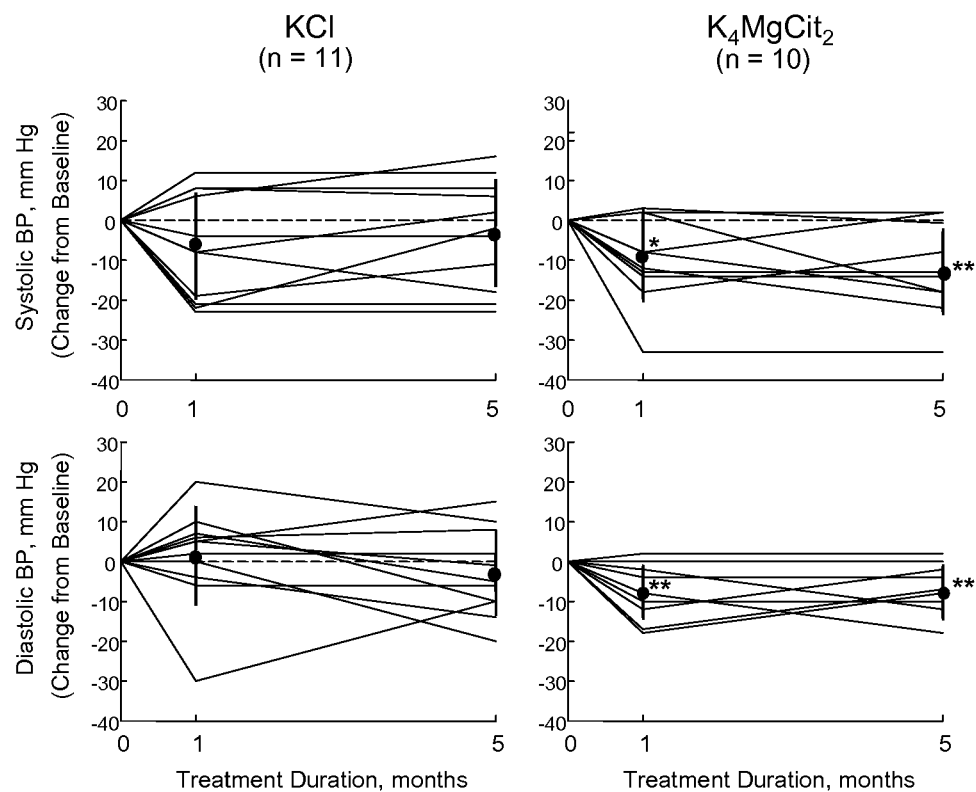
FIG. 2 graphically illustrates the effect of KMgCitrate ($K_4MgCit_2$) on blood pressure in 21 normal subjects. Changes in systolic and diastolic blood pressures from baseline (before treatment) occurring during 5 months of treatment with potassium chloride (KCl) or KMgCitrate with hydrochlorothiazide are shown individually. * $p<0.05$ from time zero, ** $p<0.01$.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "nutritionally effective amount" refers to the amount or combination of agents and amounts that will provide a beneficial nutritional effect or response in a mammal. For example, a nutritional response to hypertension using dietary supplements vary depending on age, weight, gender, disease state or states, as such, it should be understood that nutritionally effective amounts of the Potassium-Magnesium-Citrate dietary supplement and/or support for a diet that substitutes, supports or complements a DASH diet and/or additional active agents. Thus, while one mammal may require a particular profile of Potassium-Magnesium-Citrate present in defined amounts, another mammal may require the same particular profile of Potassium-Magnesium-Citrate present in different defined amounts or even via a different dosage form. For example, pediatric or geriatric patients may prefer to receive the dietary supplement as a liquid or soft gel.

As used herein, the term "pharmaceutically effective" refers to that amount of KMgCitrate effective to produce the intended effect of reducing, preventing and/or hypertension. Pharmaceutical composition refers to a composition suitable for pharmaceutical use in an animal, which may be a mammal such as a human. A pharmaceutical composition of the invention will most often includes a pharmaceutically effective amount of KMgCitrate and a pharmaceutically acceptable carrier.

A dosage form for use of the KMgCitrate of the present invention may be a single compound or mixtures thereof with other compounds, e.g., a drug for treating hypertension. The compounds may be mixed together, form ionic or even covalent bonds. The KMgCitrate of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the KMgCitrate of the present invention to a patient in need of therapy that includes the KMgCitrate.

For use as a pharmaceutical, the KMgCitrate is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the KMgCitrate may be formulated to provide, e.g., maximum and/or consistent dosing for the particular form for oral, rectal, topical, intravenous injection or parenteral administration. While the KMgCitrate may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions incorporated herein by reference.

For example, the KMgCitrate may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

KMgCitrate may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

KMgCitrate may also be coupled to one or more soluble, biodegradable, bioacceptable polymers as drug carriers or as a prodrug. Such polymers may include: polyvinylpyrrolidone, pyran copolymer, polyhydroxypropylmethacrylamide-phenol, polyhydroxyethylasparta-midephenol, or polyethyleneoxide-polylysine substituted with palmitoyl residues, mixtures thereof, and the like. Furthermore, the KMgCitrate may be coupled one or more biodegradable polymers to achieve controlled release of the KMgCitrate, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the KMgCitrate and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble KMgCitrate, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propyl-paraben, and/or chlorobutanol. Suitable pharmaceutical carriers are described in Remington's Pharmaceutical Sciences, Mack Publishing Company, a standard reference text in this field, relevant portions incorporated herein by reference.

Capsules. Capsules may be prepared by filling standard two-piece hard gelatin capsules each with 10 to 500 milligrams of powdered KMgCitrate, 5 to 150 milligrams of lactose, 5 to 50 milligrams of cellulose and 6 milligrams magnesium stearate.

Soft Gelatin Capsules. A mixture of KMgCitrate is dissolved in a digestible oil such as soybean oil, cottonseed oil or olive oil. The KMgCitrate is prepared and injected by using a positive displacement pump into gelatin to form soft gelatin capsules containing, e.g., 100-500 milligrams of KMgCitrate. The capsules are washed and dried.

Tablets. A large number of tablets are prepared by conventional procedures so that the dosage unit was 100-500 milligrams of KMgCitrate, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the KMgCitrate, conventional beading or filling agents and, optionally, sweeteners, flavors and lubricants.

Injectable solution. A parenteral composition suitable for administration by injection is prepared by stirring 1.5% by weight KMgCitrate in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain 100 mg of finely divided KMgCitrate, 200 mg of sodium carboxymethyl cellulose, 5 mg of sodium benzoate, 1.0 g of sorbitol solution, U.S.P., and 0.025 ml of vanillin.

For mini-tablets, the KMgCitrate is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

Action of Potassium-Magnesium Citrate. Studies, already conducted in normal subjects and patients with stones, will be described below. The conviction that the same effects should be displayed when given to patients with essential hypertension forms the basis of this invention.

Physical, chemical and pharmaceutical properties. KMgCitrate is a tablet formulation of pure tetrapotassium monomagnesium dicitrate, which has an empirical formula shown in FIG. 1. It provides about 5-10 mEq potassium, 2.5-5 mEq magnesium, and 7.5-15 mEq citrate per tablet. It is embedded in wax matrix to ensure a slight delay in release of its active components.

Human pharmacokinetics & bioavailability. The bioavailability of potassium and magnesium and the citraturic response from KMgCitrate were determined in 15 normal volunteers (Koenig et al., J Urol 145: 330-334, 1991). After stabilization on a metabolic diet, each subject ingested a single load of a test medication followed by timed urine collections for the next 24 hours. Test loads included KMgCitrate (49 mEq potassium, 24.5 mEq magnesium, and 73.5 mEq citrate), potassium citrate (50 mEq), potassium chloride (50 mEq), and magnesium citrate (25 mEq). Urinary potassium, magnesium, and citrate were measured for each collection period.

The peak excretion rate of urinary potassium for KMgCitrate was comparable to that of potassium citrate and potassium chloride. The peak time (time to reach peak excretion rate) was also comparable between KMgCitrate and other potassium salts at about 4 hours. The cumulative increment in urinary potassium, measured by subtracting urinary potassium following magnesium citrate dosing, gave a measure of cumulative potassium absorption for the potassium salts. Thus, potassium from KMgCitrate was just as bioavailable as that from potassium citrate or potassium chloride.

The peak excretion rate and peak time of urinary magnesium were comparable between KMgCitrate and magnesium citrate. The cumulative increment in urinary magnesium, determined by subtracting urinary potassium following potassium citrate (control), was equivalent between KMgCitrate and magnesium citrate. Thus, KMgCitrate provided an equivalent potassium bioavailability as potassium citrate and potassium chloride, and a comparable magnesium bioavailability as magnesium citrate.

Physiological and physicochemical action. Physiological and physicochemical effects of KMgCitrate were assessed in 5 normal volunteers and 5 patients with stones, while they were maintained on a constant metabolic diet (Pak et al., J Bone Min Res 7: 281-285, 1992). During KMgCitrate therapy, urinary pH, potassium, and citrate rose from the control phase. KMgCitrate reduced urinary saturation of calcium oxalate (activity product) and uric acid (content of undissociated uric acid). KMgCitrate also increased the inhibitor activity of brushite and calcium oxalate (stone-forming salts). Potassium citrate therapy did not augment urinary magnesium excretion, and did not raise pH or citrate as much. Thus, KMgCitrate reduced the propensity for the formation of calcium oxalate and uric acid stones.

Effect of KMgCitrate on kidney stone (calcium oxalate) formation. A prospective double-blind study of 64 patients with a mixed etiology of uncomplicated calcium oxalate stone disease was conducted, wherein they were randomly assigned to take KMgCitrate (42 mEq K, 21 mEq Mg/day) or placebo for up to 3 years (Ettinger et al., J Urol 158: 2069-2073, 1997). The outcome was based on survival, or percentage of patients remaining free of stones. New calculi formed in 63.6% of patients receiving placebo, and 12.6% of patients receiving KMgCitrate. When compared with placebo, the relative risk of treatment failure for KMgCitrate was 0.16 (95% confidence interval of 0.05-0.46). Thus, KMgCitrate was highly effective in preventing calcium stone formation.

Correction of hypokalemia (low blood potassium) from thiazide therapy. Normal subjects took hydrochlorothiazide 50 mg/day for 3 weeks (or 1-2 weeks if hypokalemia developed earlier). They were then randomized to take KMgCitrate or other supplements for 3 weeks while continuing on thiazide. In this study format, 62 subjects received KMgCitrate at a dose of 49 mEq K, 24.5 mEq Mg/day (Ruml et al., Am J Kid Dis 34:107-113, 1999). Serum potassium concentration decreased significantly to below the normal range in most subjects on thiazide alone. It increased significantly during supplementation with KMgCitrate, reaching normal limits in 81.7% of determinations.

The ability of KMgCitrate to correct hypokalemia during thiazide treatment was compared with that of potassium chloride at the same potassium dose of 42 mEq/day (Wuermser et al., Kid Int 57: 607-612, 1999). In both groups, serum potassium concentration decreased significantly on thiazide alone. Serum potassium concentration increased significantly to the normal range on both potassium supplementations. The rise in serum potassium on thiazide alone was indistinguishable between KMgCitrate and potassium chloride. Thus, KMgCitrate is just as effective as potassium chloride in correcting hypokalemia.

Correction of hypomagnesemia (low blood magnesium) from thiazide therapy. In the above trial comparing KMgCitrate with potassium chloride, the serum magnesium concentration increased significantly during all three weeks of KMgCitrate administration. In the potassium chloride group, serum magnesium concentration did not change significantly or decreased marginally. These changes were statistically significantly different between the two groups at corresponding time periods of supplementation. Thus, KMgCitrate can prevent or correct hypomagnesemia occurring from thiazide treatment.

Thirty subjects had hypomagnesemia (≤1.8 mg/dl) on thiazide alone. Serum magnesium concentration was significantly lower during thiazide alone than before treatment. During KMgCitrate supplementation (21.0-24.5 mEq Mg/day) for three weeks while continuing on thiazide, serum magnesium concentration increased significantly from thiazide alone, normalizing in most subjects (Pak, Clin Nephrol 59: 271-275, 2000). The percentage of subjects with hypomagnesemia decreased significantly during KMgCitrate treatment to less than 5% after three weeks of supplementation. Thus, in patients who are taking diuretics for the control of hypertension, KMgCitrate can avert hypomagnesemia.

Normal serum electrolytes. It has been suggested that diuretic-induced hypokalemia and hypochloremic alkalosis (alkali accumulation in the body with low blood chloride) may be difficult to correct by potassium supplements that does not contain chloride. This finding has been explained by an impaired reabsorption of potassium and enhanced reabsorption of bicarbonate in the kidneys in the setting of severe chloride depletion. However, when urinary chloride concentration exceeds 15 mEq/day (that is, in the absence of chloride depletion), the renal tubular reabsorption of potassium and bicarbonate is apparently intact. Because of adequate dietary chloride intake, a severe chloride deficiency is now uncommon, except in chronic diarrheal states, protracted vomiting and gastric suction. Urinary chloride exceeded 50 mEq/day in vast majority of subjects participating in past trials with KMgCitrate or in patients with renal stones or osteoporosis taking thiazide in the inventor's laboratory, indicative of adequate chloride intake. Thus, serum electrolytes were maintained within normal limits in virtually all the patients maintained on thiazide and KMgCitrate (Odvina et al., Kid Int 63: 240-247, 2003), suggesting that KMgCitrate can be used to manage hypertension without worrying about hypochloremic alkalosis.

Utility of KMgCitrate in Hypertension: Similarity of KMgCitrate with the DASH Diet KMgCitrate should share the blood pressure-lowering properties of the DASH diet, by virtue of its possessing the same key ingredients—potassium, magnesium and alkali load. This conviction is based on the knowledge gained by the inventor from studying KMgCitrate in the prevention of kidney stones and management of low blood potassium and magnesium during diuretic treatment.

KMgCitrate is a tablet formulation of a new compound with an empirical formula of $K_4MgCit_2$. Its potassium bioavailability is equivalent to that of potassium chloride and potassium citrate, and it enjoys the same magnesium bioavailability as magnesium citrate. At the same dose of potassium, KMgCitrate provides a greater alkali load than potassium citrate, increasing urinary pH and citrate. At a usual dosage, KMgCitrate delivers about 40 mEq potassium, 20 mEq magnesium and 60 mEq citrate. It is well tolerated, with a low side effect profile.

The mineral composition of KMgCitrate are compared with that of the DASH diet (expressed as the difference from the control diet, derived from the literature) in Table 1. At the usual dosage schedule, KMgCitrate delivers lower amounts of potassium, magnesium and alkali load than the recommended (strictly followed) DASH diet.

TABLE 1

Mineral Composition of KMgCitrate and DASH Diet

|  | KMgCitrate | DASH Diet* (difference from from Control Diet) |
|---|---|---|
| Potassium, mEq/day | 40 | 77 |
| Magnesium, mEq/day | 20 | 28 |
| mg/day | 243 | 340 |
| Ash Content, mEq/day | 60 alkaline | 105 alkaline |

*Mineral composition of the DASH diet represents idealized values, derived as the difference between the published compositions of recommended (strictly followed) DASH diet and the control diet (Lin et al., J Am Diet Assoc 103: 488–496, 2003).

The usual dose of KMgCitrate yielded comparable physiological effects as the DASH diet actually followed by patients derived from various published trials. Table 2 shows the values for urinary potassium and magnesium during the DASH diet from the available literature. The increment in urinary potassium during the DASH diet from the control diet was comparable to that obtained following administration of KMgCitrate delivering 42-49 mEq K per day. Likewise, urinary magnesium during the DASH diet was similar to that obtained after taking KMgCitrate. Thus, despite higher amounts of potassium and magnesium provided by the recommended DASH diet (Table 1), the actual urinary excretions of potassium and magnesium were comparable to those derived from KMgCitrate containing lower amounts of potassium and magnesium. The results suggest that in actual practice the patients actually ingest lower amounts of these cations during the DASH diet than recommended, reflective of poor compliance to the diet.

TABLE 2

Changes Produced by DASH Diet and KMgCitrate

| Authors | Potassium in mEq/day DASH | KMgCitrate | Increment in Urinary Magnesium, mg/day DASH | KMgCitrate |
|---|---|---|---|---|
| Sacks | 40 | | | |
| Conlin | 15 | | | |
| Lin | 43 | | | |
| Appel | 19 | | | |
| Nowson | 36 | | 57 | |
| Resnick | 12–18 | | 18–23 | |
| Ruml, 49 mEq K qd | | 33 | | 38 |
| Pak, 49 mEq K qd | | 51 | | 44 |
| Odvina, 42 mEq K qd | | 30–50 | | 57–63 |

Appel et al., J Am Med Ass 289: 2083–2093, 2003.
Conlin et al., Am J Hypert 16: 337–342, 2003.
Lin et al., J Nut 133: 488–496, 2003.
Nowson et al., Am J Clin Nutr 81: 983–989, 2005.
Odvina et al., Am J Therp 13: 101–108, 2006.
Pak et al., J Bone Min Res 7: 281–285, 1992.
Resnick, Am J Hypert 13: 956–965, 2000.
Ruml et al., Am J Kid Dis 34: 107–113, 1999.
Sacks et al., N Engl J Med 344: 3–10, 2001.

The inventor was unable to locate published values for urinary pH or citrate during the DASH diet. However, the DASH diet almost surely has a high content of alkaline ash, since it is rich in fruits and vegetables that are low in chloride, and high in citrate and/or potassium. Thus, it is most likely that the DASH confers urinary alkalinization and increases urinary citrate, as does KMgCitrate.

Pathophysiologic Relationship between Essential Hypertension, Metabolic Syndrome and Nephrolithiasis. There is considerable evidence suggesting that essential hypertension may be associated with other disease conditions, representing one component of the metabolic syndrome. About 70% of hypertensive subjects may suffer from insulin resistance, a characteristic feature of type II diabetes (Harano et al., J Diab Its Compl 16: 19-23, 2002). Recent studies by the investigator's laboratory indicated that idiopathic uric acid nephrolithiasis (or gouty diathesis as originally termed) may be pathogenetically linked with obesity (Maalouf et al., Kid Inter 65: 1422-1425, 2004), insulin resistance and type II diabetes (Abate et al., Kid Int 65: 386-392-2004). Moreover, renal hypercalciuria (high urinary calcium from impaired reabsorption of calcium by kidneys) has been described in some patients with essential hypertension (Strazullo et al., Clin Sci 65: 137-141, 1983).

There is some evidence that salt sensitivity (or exaggerated sodium retention by the body) may be causally important in the aforementioned clinical conditions. Salt sensitivity is common in essential hypertension and metabolic syndrome. In obese rats, salt load provokes insulin resistance and hypertension (Pamidimukkala et al., Clin Exper Hypert 26: 55-67, 2004). In Dahl salt-sensitive rats, salt loading causes insulin resistance (Ogihara et al., Hypert 40: 83-89, 2002).

Insulin resistance so produced may cause gouty diathesis with uric acid stones. The hallmark of gouty diathesis with uric acid stones is unusually acid urine that cannot be explained by intestinal alkali loss or overindulgence with acid-producing animal proteins (Khatchadurian et al., J Urol 154: 1665-1669, 1995). The inventor's laboratory pioneered studies linking gouty diathesis with the metabolic syndrome (Sakhaee et al., Kid Int 62: 971-979, 2002). A careful metabolic study disclosed impaired responsiveness to insulin in gouty diathesis (Abate et al., Kid Int 65: 386-392, 2004). Insulin resistance can cause low urinary pH by affecting sodium-hydrogen exchanger and the production of ammonium by the kidneys (Klisic et al., Am J Physiol 283: F 532-F539, 2002). Among patients with kidney stones, urinary pH was found to be inversely correlated with body weight (Maalouf, Kid Inter 65: 1422-1425, 2004), suggesting the following scheme for uric acid stone formation in gouty diathesis: obesity (or excessive food intake)→insulin resistance→unusually acid urine→uric acid stones.

A high sodium load may cause hypercalciuria in normal subjects (Breslau et al., J Clin Endo Metab 54: 369-373, 1982). Since many patients with essential hypertension have salt sensitivity, they should be expected to display an exaggerated urinary calcium loss during salt load. Renal hypercalciuria has been invoked as one of the underlying mechanisms for essential hypertension (Strazullo et al., Clin Sci 65: 137-141, 1983). Urinary calcium is sometimes high in some patients with diabetes mellitus, a condition that is considered a part of the metabolic syndrome. Hypercalciuria so-encountered can be ameliorated by insulin administration (Raskin et al., Clin Endo 9: 329-335, 1978).

Figure 3:
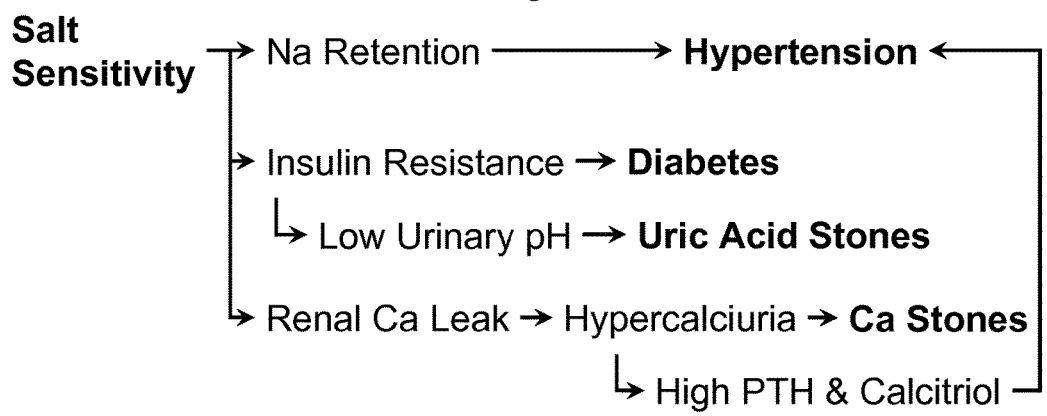
FIG. 3 graphically illustrates how salt sensitivity may cause high blood pressure, insulin resistance with uric acid stones, and hypercalciuria with calcium stones. All these abnormalities are correctable by KMgCitate.

From the preceding discussion, this invention proposes the following pathogenetic scheme linking essential hypertension with the metabolic syndrome and kidney stones (FIG. 3). The common denominator is salt sensitivity. First, salt retention leads to hypertension, by volume expansion and its associated changes. Second, salt sensitivity contributes to insulin resistance, which produces unusually acid urine by blocking the ability of insulin to produce ammonium in the kidneys. Low solubility of uric acid in an acid environment leads to uric acid stones. Lastly, salt retention produces renal hypercalciuria, increasing the propensity for calcium oxalate stone formation and stimulating the synthesis of blood pressure-raising parathyroid hormone and calcitriol (active form of vitamin D).

Expected Amelioration of Metabolic Disturbances and Clinical Improvement by KMgCitrate. In this invention, claims are made that KMgCitrate should correct various metabolic disturbances and should therefore ameliorate essential hypertension and associated clinical disorders, by affecting every step in the scheme shown in FIG. 3. The common denominator of sodium retention should be relieved by the natriuretic effect (sodium loss in urine) of potassium and alkali provided by KMgCitrate (Smith et al., J Amer Soc Nephr 2: 1302-1309, 1992; Akita et al., Hypert 42: 8-13, 2003). Magnesium from KMgCitrate might directly lower blood pressure by dilating blood vessels.

It is proposed that magnesium provided by KMgCitrate should ameliorate the insulin resistance. Normal subjects in the lower half of serum magnesium concentration had relative insulin resistance compared with those in the upper half (Rosolova et al., J Clin Endo Metab 82: 3783-3785, 1997). In a preliminary study from the inventor's laboratory, KMgCitrate improved insulin responsiveness determined by a hyperinsulinemic euglycemic pump study, as discussed in Example 3 (Abate et al., Kid Int 65: 386-392, 2004). Moreover, KMgCitrate is an effective alkalinizing agent (Ruml et al., Am J Kid Dis 6: 107-113, 1999; Pak et al., J Bone Min Res 7: 281-285, 1992). Thus, it should directly increase urinary pH and thereby inhibit uric acid stone formation.

The effect of KMgCitrate on renal hypercalciuria is less certain. The alkali load from KMgCitrate should reduce urinary calcium excretion. The inventor's laboratory was the first to show that potassium alkali reduces urinary calcium, whereas potassium chloride has no effect (Sakhaee et al., Kid Intern 24: 348-352, 1983). This finding was confirmed by other workers (Lemann et al., Kid Inter 35: 688-695, 1989; Sebastian et al., N Engl J Med 330: 1776-1781, 1994). Moreover, the hypercalciuria provoked by salt load is attenuated by potassium alkali (Sellmeyer et al., J Clin Endo Metab 87: 2008-2012, 2002). However, the magnesium load may oppose the hypocalciuric action of alkali.

Despite uncertain changes in urinary calcium, KMgCitrate should be effective in averting the risk of calcium oxalate stones from renal hypercalciuria. By providing an alkali load, KMgCitrate substantially enhances urinary excretion of citrate (Pak et al., J Bone Min Res 7: 281-285, 1992), a potent inhibitor of calcium oxalate crystallization. In a randomized trial, KMgCitrate dramatically reduced the stone formation rate among patients with calcium oxalate nephrolithiasis (Ettinger, J Urol 158: 2069-2073, 1997).

Much of the physiological-biochemical effects of KMgCitrate had been derived in normal subjects and patients with stones. We fully expect KMgCitrate should exert the same actions in patients with essential hypertension, the target of this invention.

EXAMPLE 1

Changes in Blood Pressure During KMgCitrate Treatment

In the recently published study by Odvina et al. (Am J Therap 13: 101-108, 2006) that examined the value of KMgCitrate in the prevention of thiazide-induced hypomagnesemia, the unpublished data on blood pressure were extracted. Twenty-one normal subjects participated in the trial. All were started on hydrochorothiazide 50 mg/day. Ten subjects took simultaneously KMgCitrate at a dose of 42 mEq K and 12 mEq Mg per day, while 11 subjects received potassium chloride (42 mEq/day). Supine blood pressures were taken before and each month for 5 months. FIG. 3 compares the systolic and diastolic blood pressures between the two groups.

There was a trend for systolic and diastolic blood pressures to decrease in both groups but the fall in both systolic and diastolic blood pressure was significant only in the KMgCitrate group. Thus, data suggested that KMgCitrate has a blood-lowering action beyond that of potassium chloride, which is evident in one month and lasts as long as five months. Urinary sodium was similar between the two groups.

EXAMPLE 2

Improvement of Insulin Responsiveness by KMgCitrate

In two subjects with uric acid stones, insulin responsiveness was determined before and after KMgCitrate treatment (49 mEq K, 24.5 mEq Mg per day for 4 weeks) by a hyperinsulinemic euglycemic pump procedure. During intravenous infusion of insulin, glucose was infused at a rate sufficient to maintain a constant glucose concentration. Insulin responsiveness was determined from the glucose disposal rate. The glucose disposal rate increased from 3.2 $mg/m^2/min$ before KMgCitrate to 4.3 $mg/m^2/min$ after KMgCitrate treatment in one patient. In the second patient, glucose disposal rate increased from 2.2 $mg/m^2/min$ to 2.8 $mg/m^2/min$. Thus, KMgCitrate treatment improved insulin responsiveness, or rendered treated patients less insulin resistant.

KMgCitrate is expected to provide amelioration of other biochemical-physiological disturbances of metabolic syndrome when given to patients with essential hypertension as previously described in normal subjects and patients with kidney stones. Thus, in patients with essential hypertension (target population of this invention), KMgCitrate should provide alkali load and increased urinary pH (Sakhaee et al., J Clin Endoc Metab 72: 396-400, 1991; Ruml et al., Amer J Kid Dis 34:107-113, 1999), reduce propensity for calcium stone formation (Koenig et al., J Urol 145: 330-334, 1991), and improve magnesium status (Pak, Clin Nephrol 59: 271-275, 2000). In hypertensive patients taking diuretics, KMgCitrate should prevent hypokalemia and hypomagnesemia as shown in normal subjects and patients with stones.

Table 3 summarizes the salient distinction between this invention and other patents. KMgCitrate taught herein is the only one that is a single compound containing potassium, magnesium and citrate without other cations or anions, to be used as a pharmaceutical preparation in human beings for the management of essential hypertension and correction of biochemical abnormalities of metabolic syndrome.

TABLE 3

| | Distinction Between This Invention and Other Patents | | | | | | |
|---|---|---|---|---|---|---|---|
| | Single/ Mixture | K & Mg | Other cation | Citrate and Alkali | Chloride or Sulfate | Experimental animal or Human | Seasoning/ pharmaceutical Preparation | Hypertension, process or diet supplement |
| U.S. Pat. No. 5,432,200 & U.S. Pat. No. 5,219,889 | Single | Yes | No | Yes | No | Human | Pharma-ceutical | Process, supplement |
| U.S. Pat. No. 7,091,246 B2 | Single | Yes | No | Yes | No | None | Pharma-ceutical | Process |
| PCT/SE89/00410 and PCT/EP94/03072 | Single | Yes | No | No | Yes | Human | Salt substitute | Variable Na intake in hypertension study |
| U.S. Pat. No. 2004/0224076 A1 | Mixture | Yes | Yes | No | Yes | None | Salt substitute | Diet supplement |
| U.S. Pat. No. 6,136,349 | Mixture | Yes | Yes | No | Yes | Rats | Seasoning | Rats |
| U.S. Pat. No. 2005/0123670 A1 | Liquid | Yes | Yes | No | Yes | None | Seasoning | Supplement |
| PCT/US2004/006349 | Mixture | Yes | Yes | No | Yes | None | Salt substitute | Process |
| U.S. Pat. No. 6,881,750 B2 | Single | No Mg | No | No citrate | No | Rats | Both | Blood pressure study in rats |
| JP1300874 | Mixture | Yes | Yes | Unknown | Unknown | None | Food additive | Supplement |
| JP6343417 | Mixture | Yes | Yes | No | Yes | Unknown | Seasoning | Supplement |
| CN1090483C | Single | Yes | No | No | Yes | Human | Pharma-ceutical | Supplement |
| This invention | Single | Yes | No | Yes | No | Human | Pharma-ceutical | Hypertension |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Patent Documents

U.S. Pat. No. 5,432,200. Jul. 11, 1995. Walsdorf, Alexandrides and Pak. Method for increasing urinary excretion of electrolytes.

U.S. Pat. No. 5,219,889. Jun. 15, 1993. Walsdorf, Alexandrides and Pak. Dietary supplementation with potassium magnesium citrate.

U.S. Pat. No. 7,091,246 B2. Aug. 15, 2006. Dietary supplementation with stoichiometrically specific potassium magnesium citrate.

PCT/EP94/03072. Sep. 14, 1994. De Jong & Grobbee. Salt composition.

PCT/SE89/00410. Jul. 13, 1989. Sundstrom. Salt product and method for its preparation.

US 2004/0224076 A1. Nov. 11, 2004. Derrien & Fontvieille. Dietary composition in the form of a salt substitute for table salt.

U.S. Pat. No. 6,136,349. Oct. 24, 2000. Karppanen, Karppanen, Karppanen, Nevalainen & Vaskonen. Food seasoning, food ingredients and food item compositions and methods for their preparation.

US 2005/0123670 A1. Jul. 9, 2005. Vasquez. Stable sodium-free or low-sodium aqueous solution of agreeable saltiness taste.

PCT/US2004/006349. Mar. 3, 2004. Vasquez. Non-bitter sodium-free or low-sodium salt composition.

U.S. Pat. No. 6,881,750 B2. Apr. 19, 2005. Boynton. Potassium tartrate bicarbonate and ascorbate.

JP1300874. Dec. 5, 1989. Takashi, Masahiko, Yasuyuki & Yoshiro. Special nourishing food.

JP6343417. Dec. 20, 1994. Bunsuki & Hideyuki. Salted seasoning.

CN1090483C. Sep. 11, 2002. Xie Lifeng. Potassium and magnesium slow-release tablet and method of producing such.

Other Documents

Abate N, Chandalia M, Cabo-Chan A V Jr, Moe O W, Sakhaee K. The metabolic syndrome and uric acid nephrolithiasis: novel features of renal manifestations of insulin resistance. Kid Int 65: 386-392, 2004.

Akita S, Sacks F M, Svetkey L P, et al. Effects of the dietary approaches to stop hypertension (DASH) diet on the pressure-natriuresis relationship. Hypertension 42: 8-13, 2003.

Appel L J, Champagne C M, Harsha D W, Cooper L S, Obarzanek E, Elmer P J, Stevens V J, Vollmer V M, Lin P H, Svetkey L P, Stedman S W, Young D R, Writing Group of the PREMIER Collaborative Research Group. Effects of comprehensive lifestyle modification on blood pressure control: main results of the PREMIER clinical trial. J Am Med Ass 289: 2083-2093, 2003.

Aviv A, Hollenberg N K, Weder A. Urinary potassium excretion and sodium sensitivity in blacks. Hypert 43: 707-713, 2004.

Breslau N A, McGuire J L, Zerwekh J, Pak C Y C. The role of dietary sodium on renal excretion and intestinal absorption of calcium and on vitamin D metabolism. J Clin Endoc Metab 55: 369-373, 1982.

Conlin P R, Erlinger T P, Bohannon A, Miller E R 3$^{rd}$, Appel L J, Svetkey L P, Moore T J. The DASH diet enhances the blood pressure response to losartan in hypertensive patients. Am J Hypert 16: 337-342, 2003.

Ettinger B, Pak C Y C, Citron J T, Thomas C, Adams-Huet B, VanGessel A. Potassium-magnesium citrate is an effective prophylaxis against recurrent calcium oxalate nephrolithiasis. J Urol 158: 2069-2073, 1997.

Harano Y, Suzuki M, Koyama Y, Kanda M, Yasuda S, Suzuki K, Takamizawa I. Multifactorial insulin resistance and clinical impact in hypertension and cardiovascular diseases. J Diab Compl 16: 19-23, 2002.

Khatchadourian J, Preminger G M, Whitson P, Adams-Huet B, Pak C Y C. Clinical and biochemical presentation of gouty diathesis: comparison of uric acid versus pure calcium stone formation. J Urol 154: 1665-1669, 1995.

Klisic J, Hu M C, Nief V, Reyes L, Fuster D, Moe O W, Ambuhl P M. Insulin activates Na(+)/H(+) exchanger 3: biphasic response and glucocorticoid homeostasis. Am J Physiol 283: F532-F539, 2002.

Koenig K, Padalino P, Alexandrides G, Pak C Y C. Bioavailability of potassium and magnesium, and citraturic response from potassium-magnesium citrate. J Urol 145: 330-334, 1991.

Lemann J Jr, Gray R W, Pleuss J A. Potassium bicarbonate, but not sodium bicarbonate, reduces urinary calcium excretion and improves calcium balance in healthy men. Kid Inter 35: 688-695, 1989.

Lin P H, Aickin M, Champagne C, Craddick S, Sacks F M, McCarron P, Most-Windhauser M M, Rukenbrod F, Haworth L; DASH-Sodium Collaborative Research Group. Food group sources of nutrients in the dietary patterns of the DASH-Sodium trial. J Am Diet Assoc 103: 488-496, 2003.

Maalouf N M, Sakhaee K, Parks J H, Coe F L, Adams-Huet B, Pak C Y C. Association of urinary pH with body weight in nephrolithiasis. Kid Int 65: 1422-1425, 2004.

Morris R C Jr, Schmidlin O, Tanaka M, Forman A, Frassetto L, Sebastian A. Differing effects of supplemental KCl and KHCO$_3$: pathophysiological and clinical implications. Semin Nephrol 19: 487-493, 1999.

Nowson C A, Worsley A, Margerison C, Jorna M K, Godfrey S J, Booth A. Blood pressure change with weight loss is affected by diet type in men. A J Clin Nutr 81: 983-989, 2005.

Ogihara T, Asano T, Ando K, et al. High-salt diet enhances insulin signaling and induces insulin resistance in Dahl salt-sensitive rats. Hypertension 40: 83-89, 2002.

Odvina C V, Preminger G M, Lindberg J S, Moe O W, Pak C Y C. Long-term combined treatment with thiazide and potassium citrate in nephrolithiasis does not lead to hypokalemia or hypochloremic metabolic alkalosis. Kid Int 63: 240-247, 2003.

Odvina C V, Mason R P, Pak C Y C. Prevention of thiazide-induced hypokalemia without magnesium depletion by potassium-magnesium citrate. Am J Therap 13: 101-108, 2006.

Pak C Y C. Koenig K, Khan R, Haynes S, Padalino. Physicochemical action of potassium-magnesium citrate in nephrolithiasis. J Bone Miner Res 7:281-285, 1992.

Pak C Y C. Correction of thiazide-induced hypomagnesemia by potassium-magnesium citrate from review of prior trials. Clin Nephrol 59: 271-275, 2000.

Pamidimukkala J & Jandhyala B S. Effect of salt rish diet in the obese Zucker rats: studies on renal function during isotonic volume expansion. Clin Exper Hypert 26: 55-67, 2004.

Raskin P, Stevenson M R M, Barilla D, Pak C Y C. The hypercalciuria of diabetes mellitus: its amelioration with insulin. Clin Endoc 9: 329-335, 1978.

Resnick L M, Oparil S, Chait A, et al. Factors affecting blood pressure responses to diet: the Vanguard study. Am J Hypert 13: 956-965, 2000.

Rosolova H, Mayer O, Reaven G. Effect of variation in plasma magnesium concentration on resistance to insulin-mediated glucosa disposal in non-diabetic subjects. J Clin Endo Metab 82: 3783-3785, 1997.

Ruml L A, Pak C Y C. Effect of potassium magnesium citrate on thiazide-induced hypokalemia and magnesium loss. Amer J Kid Dis 34:107-113, 1999.

Sacks F M, Appel L J, Moore T J, Obarzanek E, Vollmer W M, Svetkey L P, Bray, G A, Vogt T M, Cutler J A, Windhauser M M, Lin P H, Karanja N. A dietary approach to prevent hypertension: a review of the Dietary Approaches to Stop Hypertension (DASH) Study. Clin Cardiol 22: III 6-10, 1999.

Sacks F M, Svetkey L P, Vollmer W M, Appel L J, Bray G A, Harsha D, Obarzanek E, Conlin P R, Miller E R $3^{rd}$, Simons-Morton D G, Karanja N, Lin P H; DASH-Sodium Collaborative Research Group. Effects on blood pressure of reduced dietary sodium and the Dietary Approaches to Stop Hypertension (DASH) diet. DASH-Sodium Collaborative Research Group. N Engl J Med 344: 3-10, 2001.

Sakhaee K, Nicar M J, Hill K, Pak C Y C. Contrasting effects of potassium citrate and sodium citrate therapies on urinary chemistries and crystallization of stone-forming salt. Kid Int 24: 348-352, 1983.

Sakhaee K, Alpern R, Jacobson H R, Pak C Y C. Contrasting effects of various potassium salts on renal citrate excretion. J Clin Endoc Metab 72: 396-400, 1991.

Sakhaee K, Harvey J A, Padalino P K, Whitson P, Pak C Y C. Potential role of salt abuse on the risk for kidney stone formation. J Urol 150: 310-312, 1991.

Sakhaee K, Adams-Huet B, Moe O W, Pak C Y C. Pathophysiologic basis for normouricosuric uric acid nephrolithiasis. Kid Int 62: 971-979, 2002.

Schmidlin O, Tanaka M, Bollen A W, Yi S L, Morris R C Jr. Chloride-dominant salt sensitivity in the stroke-prone spontaneously hypertensive rat. Hypertension 45: 867-873, 2005.

Sebastian A, Harris S T, Ottaway J H, Todd K M, Morris R C Jr. Improved mineral balance and skeletal metabolism in postmenopausal women treated with potassium bicarbonate. N Engl J Med 330: 1776-1781, 1994.

Sellmeyer D E, Schloetter M, Sebastian A. Potassium citrate prevents increased urine calcium excretion and bone resorption induced by a high sodium chloride diet. J Clin Endocrinol Metab 87: 2008-2012, 2002.

Smith S R, Klotman P E, Svetkey L P. Potassium chloride lowers blood pressure and causes natriuresis in older patients with hypertension. J Am Soc Nephr 2: 1302-1309, 1992.

Strazzullo P, Nunziata V, Cirillo M, Giannattasio R, Ferrara L A, Mattioli P L, Mancini M. Abnormalities of calcium metabolism in essential hypertension. Clin Sci (Lond) 65: 137-141, 1983.

Suter P M, Sierro C, Vetter W. Nutritional factors in the control of blood pressure and hypertension. Nutr Clin Care 5: 9-19, 2002.

Touyz R M, Milne F J, Reinach S G. Intracellular Mg2+, Ca2+, Na2+ and K+ in platelets and erythrocytes of essential hypertension patients: relation to blood pressure. Clin Exp Hypert 14: 1189-1209, 1992.

Vollmer V M, Sacks F M, Ard J, Appel L J, Bray G A, Simons-Morton D G, Conlin P R, Svetkey L P, Erlinger T P, Moore T J, Karanja N; DASH-Sodium Trial Collaborative Research Group. Effects of diet and sodium intake on blood pressure: subgroup analysis of the DASH-sodium trial. Ann Inter Med 135: 1019-1028, 2001.

Windhauser M M, Ernst D M, Karanja N M, Crawford S W, Redican S E, Swain J F, Karimbakas J M, Champagne C M, Hoben K P, Evans M A. Translating the Dietary Approaches to Stop Hypertension diet from research to practice: dietary and behavior change techniques. DASH Collaborative Research Group. J Am Diet Assoc 99: S90-95, 1999.

Witteman J C, Willett W C, Stampfer M J, Colditz G A, Sacks F M, Speizer F E, Rosner B, Hennekens C H. A prospective study of nutritional factors and hypertension among US women. Circulation 80: 1320-1327, 1989.

Wuermser L A, Reilly C, Poindexter J, Pak C Y C. Potassium-magnesium citrate versus potassium chloride in thiazide-induced hypokalemia. Kidn Intern 57: 607-612, 1999.

What is claimed is:

1. A method for ameliorating or correcting one or more metabolic disturbances in a patient having one or more metabolic disturbances and essential hypertension, wherein the one or more metabolic disturbances are selected from the group consisting of: salt retention, insulin resistance, unusually acid urine, low serum magnesium, or renal hypercalciuria, the method comprising providing to the patient a composition comprising a pharmaceutically effective amount of potassium, magnesium, and citrate.

2. The method of claim 1, wherein the patient is suffering from or at risk of suffering from type II diabetes, uric acid stones, or calcium stones.

3. The method of claim 1, wherein the molar ratio of potassium-magnesium citrate is about 4:1:2.

4. The method of claim 1, wherein the molar ratio of potassium:magnesium:citrate is about 1:1:1.

5. The method of claim 1, wherein the composition comprises 10-80 mmoles potassium, 2.5-20 mmoles magnesium, and 5-40 mmoles citrate and is administered to the patient daily.

6. The method of claim 1, wherein the metabolic disturbance is insulin resistance.

7. The method of claim 1, wherein the patient is being treated with a thiazide.

* * * * *